(12) United States Patent
Carr et al.

(10) Patent No.: US 7,426,028 B2
(45) Date of Patent: Sep. 16, 2008

(54) SPECTROSCOPIC FEEDBACK FOR HIGH DENSITY DATA STORAGE AND MICROMACHINING

(75) Inventors: Christopher W. Carr, Livermore, CA (US); Stavros Demos, Livermore, CA (US); Michael D. Feit, Livermore, CA (US); Alexander M. Rubenchik, Livermore, CA (US)

(73) Assignee: Lawrence Livermore National Security, LLC, Livermore, CA (US)

( * ) Notice: Subject to any disclaimer, the term of this patent is extended or adjusted under 35 U.S.C. 154(b) by 408 days.

(21) Appl. No.: 11/375,882

(22) Filed: Mar. 14, 2006

(65) Prior Publication Data

US 2007/0188752 A1 Aug. 16, 2007

Related U.S. Application Data

(60) Provisional application No. 60/661,685, filed on Mar. 14, 2005.

(51) Int. Cl.
*G01J 3/28* (2006.01)
(52) U.S. Cl. ........................ 356/326; 356/330; 365/120; 365/106
(58) Field of Classification Search ................ 356/356, 356/330, 328; 365/120, 127, 106, 116; 250/390.07, 250/227.23
See application file for complete search history.

(56) References Cited

U.S. PATENT DOCUMENTS

| 4,466,080 A | 8/1984 | Swainson et al. |
| 6,998,214 B2 * | 2/2006 | Fourkas et al. .............. 430/269 |
| 2007/0086309 A1 * | 4/2007 | Yang ..................... 369/112.01 |

OTHER PUBLICATIONS

Tong et al, Real-time control of ultrafast laser micromachining by laser-induced breakdown spectroscopy, Mar. 2004, Applied Optics, vol. 43, No. 9, pp. 1971-1980.*
Schaffer et al, "Morphology of Femtosecond Laser-Induced Structural Changes in Bulk Transparent Materials." Applied Physics Letters, vol. 84, No. 9, Mar. 1, 2004. @2004 American Institute of Physics.
C.W. Carr, "Experimental Studies of Laser-Induced Breakdown in Transparent Dielectrics." Sep. 23, 2003. UCRL-LR-155392 Thesis.

* cited by examiner

*Primary Examiner*—L. G Lauchman
(74) *Attorney, Agent, or Firm*—Michael C. Staggs; John H. Lee

(57) ABSTRACT

Optical breakdown by predetermined laser pulses in transparent dielectrics produces an ionized region of dense plasma confined within the bulk of the material. Such an ionized region is responsible for broadband radiation that accompanies a desired breakdown process. Spectroscopic monitoring of the accompanying light in real-time is utilized to ascertain the morphology of the radiated interaction volume. Such a method and apparatus as presented herein, provides commercial realization of rapid prototyping of optoelectronic devices, optical three-dimensional data storage devices, and waveguide writing.

45 Claims, 3 Drawing Sheets

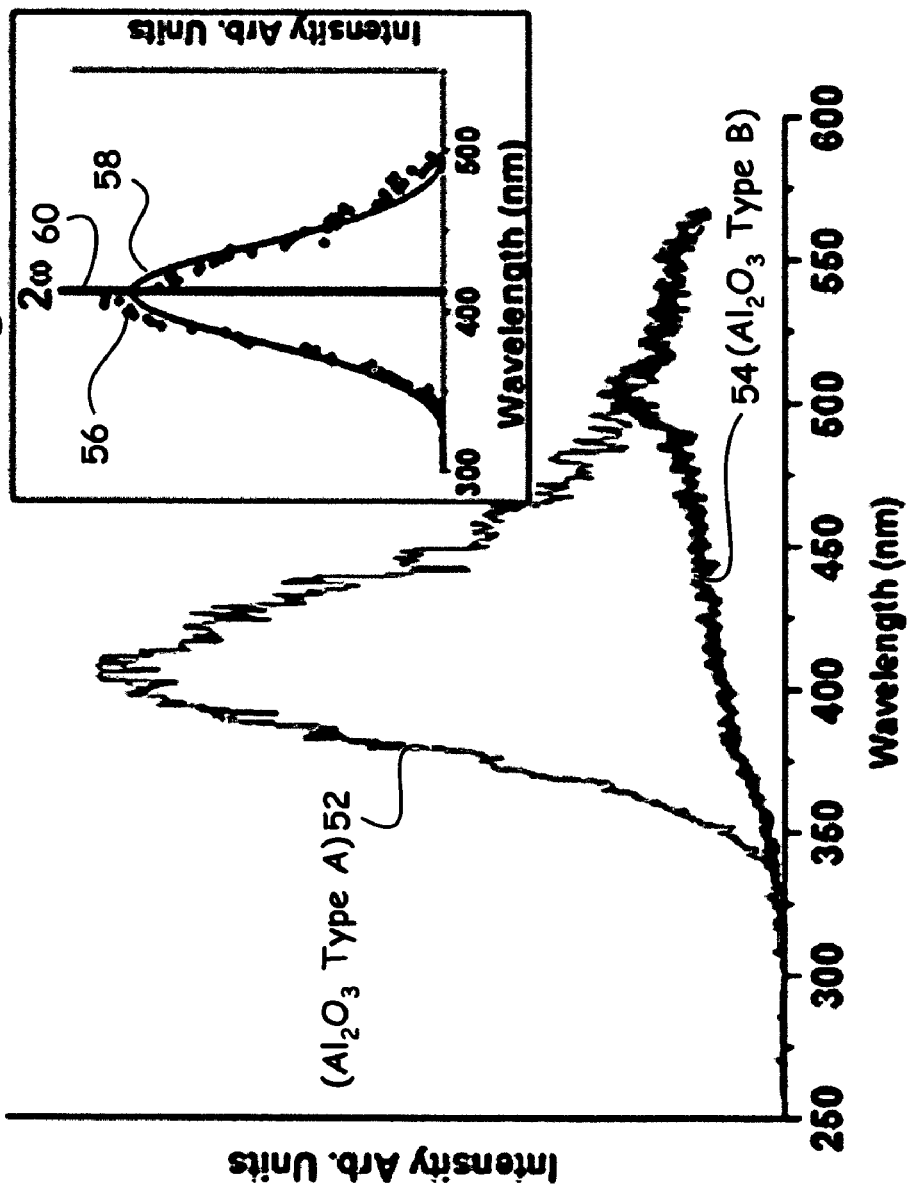

SPECTROSCOPIC FEEDBACK FOR HIGH DENSITY DATA STORAGE AND MICROMACHINING

RELATED APPLICATION

This application claims the benefit of U.S. Provisional Application No. 60/661,685, filed Mar. 14, 2005, entitled, "Time Gated Spectroscopy for Real-Time Monitoring During Laser Micromachining," which is incorporated herein by this reference.

The United States Government has rights in this invention pursuant to Contract No. W-7405-ENG-48 between the United States Department of Energy and the University of California for the operation of Lawrence Livermore National Laboratory.

BACKGROUND OF THE INVENTION

1. Field of the Invention

The present invention relates to a real-time diagnostic for determining laser induced breakdown events. More particularly, the present invention relates to an apparatus and a method that utilizes spectroscopic evaluation as a feedback means in real-time for determining optically produced three dimensional objects within an interaction volume.

2. Description of Related Art

The use of femtosecond lasers for micro-machining, waveguide writing, microfluidic applications, and three-dimensional storage is a rapidly maturing field. Laser-based techniques have several marked benefits over traditional methods including, but not limited to, rapid device prototyping, cost effective production, and its simplicity for the construction of three-dimensional devices. The use of femtosecond lasers for micromachining/microfabricating applications offers distinct benefits compared to using other types of laser based systems, such as, for example, nanosecond excimer lasers due to better control of the energy deposition process. A persistent problem in machining structures at the smallest possible scale barrier arises in adequate control of the laser-material interaction volume leading to collateral material damage.

Background information on an existing three-dimensional storage using optical methods and apparatus is described in U. S. Pat. No. 4,466,080, entitled "Three Dimensional Patterned Media," issued Aug. 14, 1984 to Sainson et al., including the following, "Method and active media for controlled production of physical and refractive index inhomogenetics in a volume of a suspension medium by use of at least two intersecting beams of electromagnetic radiation matched to the excited state properties of molecules in the media. In addition, complex three-dimensional physical and chemical structures are produced by selective excitation of different types of molecules in the media and by employing transportive capabilities of liquid or gaseous support medium." However, such techniques from the above cited patent do not address detecting and quantifying laser-induced physical damage using spectroscopic analysis as a confirming tool in accordance with the principles of the present invention.

Accordingly, a need exists for methods and apparatus that can real-time monitor localized predetermined breakdown of desired material. Such monitoring apparatus and techniques as disclosed herein, enable micromachining/microfabrication writing processes within transparent materials and/or predetermined materials transparent to a use wavelength (e.g., ceramics) while undergoing predetermined laser intensities to improve process control and improve yield. The present invention is directed to such a need.

SUMMARY OF THE INVENTION

Accordingly, the present invention is directed to a spectroscopic feedback method for writing optical data that includes: illuminating an interaction volume with predetermined laser optical intensities to define a plurality of data bits and thereby encode a data set; and spectroscopically real-time confirming a written bit status for each defined bit of the data set.

Another aspect of the present invention provides a spectroscopic feedback method for writing in an optical material that includes: micromachining an interaction volume with a predetermined laser intensity; and spectroscopically real-time confirming for a desired morphology resulting from the predetermined laser intensity.

Still another aspect of the present invention is directed to a spectroscopic apparatus that self-checks for a desired morphology in an optical material, by basically utilizing a pump source to produce a desired morphology within an interaction volume of a material and by real-time monitoring a characteristic spectral emission so as to confirm the desired morphology.

Accordingly, the present invention provides spectroscopic optical arrangements and methods to monitor the machining/microfabrication of optical devices (e.g., waveguides, optoelectronic devices, waveguides, etc.) in materials, such as, but not limited to, dielectrics, ceramics, and plastic materials. The techniques, as disclosed herein, monitors such processes in real-time so as to improve process control and therefore process yield. In addition, the ability to monitor and control the breakdown mechanism noninvasively allows modified material to be written in the different morphologies with increased precision.

BRIEF DESCRIPTION OF THE DRAWINGS

The accompanying drawings, which are incorporated into and constitute a part of the specification, illustrate specific embodiments of the invention and, together with the general description of the invention given above, and the detailed description of the specific embodiments, serve to explain the principles of the invention.

FIG. 3(a) shows a pair of emission spectra from $Al_2O_3$.

FIG. 3(b) shows the difference spectra resulting from FIG. 3(a).

DETAILED DESCRIPTION OF THE INVENTION

Figure 1:
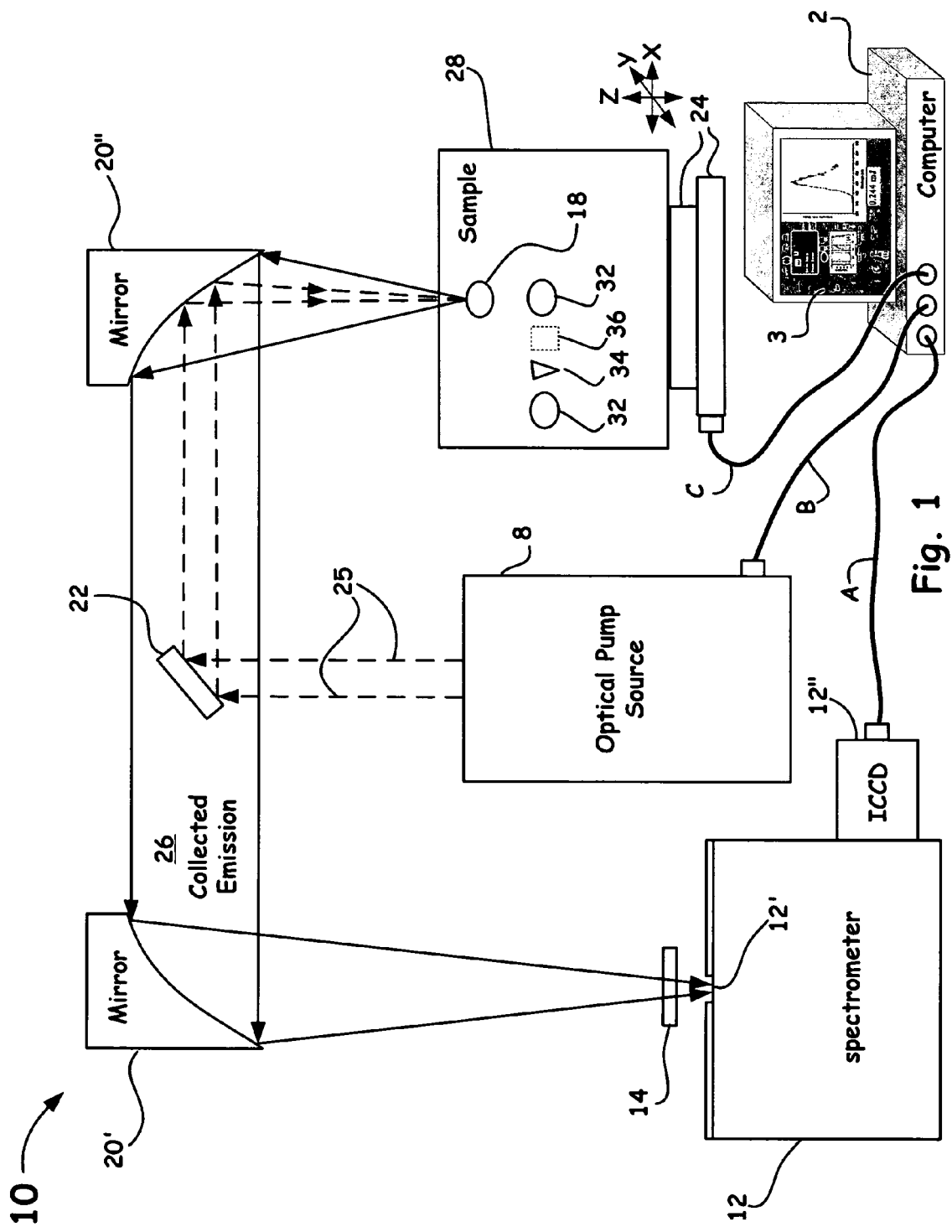
FIG. 1 shows a simplified diagram of a spectroscopic feedback apparatus of the present invention.

Referring now to the drawings, specific embodiments of the invention are shown. The detailed description of the specific embodiments, together with the general description of the invention, serves to explain the principles of the invention.

Unless otherwise indicated, all numbers expressing quantities of ingredients, constituents, reaction conditions and so forth used in the specification and claims are to be understood as being modified in all instances by the term "about". Accordingly, unless indicated to the contrary, the numerical parameters set forth in the specification and attached claims are approximations that may vary depending upon the desired properties sought to be obtained by the subject matter presented herein. At the very least, and not as an attempt to limit the application of the doctrine of equivalents to the scope of the claims, each numerical parameter should at least be construed in light of the number of reported significant digits and by applying ordinary rounding techniques. Notwithstanding that the numerical ranges and parameters setting forth the broad scope of the subject matter presented herein are approximations, the numerical values set forth in the specific examples are reported as precisely as possible. Any numerical value, however, inherently contain certain errors necessarily resulting from the standard deviation found in their respective testing measurements.

General Description

The general principle of the present invention entails inducing physical changes (i.e., a desired morphology) in optical materials while spectroscopically monitoring such changes in real-time. The methods and arrangements of the present invention, as disclosed herein, can be utilized to formulate, for example, optical channel(s) in waveguides, or as another beneficial embodiment, the present invention can be utilized to encode digitized information in a desired interaction plane and/or volume in predetermined materials, e.g., dielectrics, using breakdown intensities without substantially affecting adjacent planes.

Specifically, precise control of the breakdown process is of extreme importance for precision laser material processing applications such as laser micromachining of transparent materials and manufacturing of optical devices. Understanding how to connect laser parameters with the properties and the extent of the plasma generated by breakdown ensures the consistency of structural features and reduces unwanted collateral damage of predetermined material.

Moreover, desired breakdown intensities induced by, for example, femtosecond laser pulses, can be arranged to produce an ionized region of dense plasma confined within the bulk of selected materials. A beneficial broadband radiation that accompanies the breakdown process (i.e., radiation originating from plasma-induced second-harmonic generation, supercontinuum generation, or thermal emission) can simultaneously be monitored by methods and apparatus as disclosed herein to ascertain the morphology of the irradiated region.

A very beneficial aspect of the present invention includes using predetermined breakdown intensities to induce desired morphological changes as a means of encoding digitized information into predetermined optical materials with a density of greater than $10^9$ per cubic centimeter while confirming (i.e., real-time self-checking) the accuracy of such encoded information via the spectroscopic techniques disclosed herein. Upon confirmation, information so written can then be read using three dimensional resolution optical methods known by those skilled in the art, such as, but not limited to, laser differential interference contrast microscopy, confocal microscopy, and/or scattering microscopy.

Specific Description

Turning now to the drawings, a hardware diagram that illustrates an exemplary general embodiment of a system constructed to illustrate the principles of the present invention is shown in FIG. 1. The system, designated generally by the reference numeral 10, and capable of being designed as a portable compact apparatus, includes the following basic components: a processor 2, a pump source 8, a spectroscopic means 12, directional optical elements 22, 20', and 20", X-Y-Z (denoted with arrows) translation stages 24, one or more filtering optics 14, and a desired optical sample 28 for micromachining and, or optical data storage.

In addition to hardware, a control system software such as, but not limited to, Fortran, Basic, Visual Basic, LabVIEW, Visual C++, C++, or any programmable language, often a graphical programming environment, capable of operating within the scope and spirit of the invention herein can be utilized within system 10. LabVIEW in particular, is specifically tailored to the development of instrument control applications and facilitates rapid user interface creation and is particularly beneficial as an application to be utilized in the present invention. A single user interface (e.g., a graphical interface control means 3, as shown in FIG. 1) permits a user to choose predetermined fluences for a desired write or micromachining application, manually position sample 28 via translation stages 24 to a desired X-Y-Z coordinate or series of coordinate positions via processor 2 directed commands along configured computer interfaces (e.g., RS232 or USB communication cables A, B, C) to create a custom optical device (e.g., a waveguide) and/or to create a three dimensional array of optical created structured sites that can be utilized as an optical data storage element.

In an example method of the invention, a pre-selected optical sample 28, can be irradiated for creating waveguide structures or for data storage through a predetermined refractive focusing optical element, such as, a high numerical aperture (N.A.) objective lens (not shown) to achieve predetermined fluences of up to about 10 J/cm$^2$. However, it is more often desirable to an off-axis parabolic mirror 20" configured to receive pump radiation 25 from a reflective optical element 22 and capable of focusing to the required dimensions so as to create desired irradiation intensities in a given sample 28. As another arrangement, computer controlled scanning reflective optics (not shown) coupled with refractive and/or reflective optical components focusing elements, such as an off-axis parabolic mirror 20", can also be utilized to direct one or more pulses from an electromagnetic radiation pump source 8 (e.g., a pulsed laser) to one or more predetermined sites within the volume of sample 28. Beneficial pump sources 8, often are arranged to have pulse widths of greater than about 1 fs pulses, a wavelength greater than about 200 nm (more often of about 820 nm wavelength light from a Ti:sapphire laser), and designed to emit desired intensities that can be optically manipulated so as to direct fluences of up to about 10 J/cm$^2$ to one or more predetermined sites in sample 28. As another arrangement, a focused pump source beam 25 can be stationary but the sample 10 can be translated to one or more desired locations via configured stepper motor driven X-Y-Z stages 24. Such an arrangement enables a user to position sample 28 to one or more desired locations for irradiation automatically via software (e.g., graphical interface control means 3) commands through a processor 28 (e.g., a desktop computer, a laptop computer) to enable, for example, encoding information in an optical material by the methods disclosed herein.

Therefore, by moving the pump source beam 25 in an X-Y direction via scanning mirror configurations (not shown) and/or by translating sample 28 under a stationary pump source beam 25 as described above via X-Y-Z stages 24, and by dialing in predetermined breakdown fluences for a known sample material, a waveguide structure or a two-dimensional bit plane can be defined along predetermined transverse locations. In a three-dimensional data storage application, moving the sample 28 in the Z direction or positioning the focused pump source beam 25 in the Z direction at different planes enables predetermined two-dimensional bit planes to also be defined so that three-dimensional stacks of data having a density of greater than about 10$^9$ bits per cubic centimeter can be written into sample 28. Because the volume of the written bit depends on $1/(N.A.)^4$, the use of high numerical aperture focusing optics is desired to maximize data density.

Micromachining in a waveguide application occurs when the emission from pump source 8, having a wavelength and pulsewidth designed for the sample, is focused at a location in the sample with a predetermined intensity above the critical breakdown power (Pcr) threshold, as detailed below, of sample 28. Such an application modifies the morphology of the interaction volume of the sample via structural modification by way of optical self-focusing (i.e., filamentation) so as to create cone-like structures (e.g., reference numeral 34 as shown in FIG. 1) pointing along the direction of propagation with the cone angle being defined by the numerical aperture of the focusing element (i.e., a smaller numerical aperture having a larger cone angle). Such structures can be micromachined/microfabricated to have predetermined lengths of greater than about 1 micron along the longest dimension as determined by illumination intensities above a critical breakdown power (Pcr), as detailed below, which is a function of the illumination wavelength for a given material. Using such predetermined breakdown intensities above the critical breakdown intensity results in a modification of the material that is characteristically different (e.g., structurally different and having a different refractive index) than surrounding material outside the breakdown region of beam pump source 8. Writing in a data storage application occurs when the light focused at a location in the sample results in the optical self-focusing process as described above but may also occur with a predetermined intensity at or slightly above the breakdown threshold of sample 28 so as to modify the morphology, also via structural modification, as determined by the focal volume of a given focusing optical element, such as, for example, off-axis parabolic mirror 20", a refractive optic having a high numerical aperture, or any refractive or reflective optical element capable of operating within the parameters of the present invention. Such intensities that are at or slightly above threshold often result in disk-like structures (e.g., reference numeral 32 as shown in FIG. 1) of, fro example, less than about 1 micron in the longest dimension, which are also characteristically different than surrounding material (structurally and with a different index of refraction) outside the breakdown region of beam pump source 8 but in either breakdown writing embodiment, the desired structural changes can be designed as a desired data bit (e.g., a digital 1 or a digital 0). As another arrangement, a predetermined coordinate site 36 (as shown by a dashed square) within the two or three-dimensional stack of data sites can be chosen wherein no breakdown occurred (e.g., by not illuminating with a breakdown intensity) so as to represent a digital 0, wherein a digital 1 can be represented by either structural change (e.g., disk-like structures 32 or cone-like structures 34) as detailed above. Thus, the present invention is capable of $3^2$ amount of digital data representation.

A novel aspect and surprising unexpected result of the present invention is the associated spectra during the creation of the structures detailed above so as to provide a means to confirm in real-time, the writing of such structures. In particular, the optical breakdown of desired samples (e.g., dielectrics, materials transparent to a use wavelength (e.g., ceramics)) of the present invention using optical pulses that are greater than about 1 femtosecond produces an ionized region of dense plasma confined within the bulk of the chosen material. Such an ionized region is responsible for broadband radiation that accompanies the breakdown process. Spectroscopic measurements of the accompanying light have been used to show, depending on the laser parameters, that the spectra may originate from plasma-induced second-harmonic generation, supercontinuum generation, or thermal emission by the plasma. By monitoring the emission from the ionized region using, for example, the techniques and configurations of the present invention, such as, the example configuration of FIG. 1, the predominant breakdown mechanism and thus, the associated morphology of the damage region can be substantially controlled and determined in real-time as a confirming means of verifying the creation of such structures.

To best illustrate the surprising and unexpected spectroscopic aspects of the present invention, the following experimental method and results, which is intended to be only illustrative of the present invention, is described below with respect to the example configuration of FIG. 1.

To illustrate the present invention, a configured Ti:sapphire laser (i.e., optical pump source 8) having a 190 fs pulse duration and a wavelength of about 820 nm with a bandwidth of about 10 nm was implemented as optical pump source 8. A mechanical shutter (not shown) isolated single pulses from the output of a 100 Hz pulse train, so as to produce peak fluences of about 5 J/cm$^2$ for the output pulses and a power level on the order of about 4 MW. Such pulses were directed along an optical pump source path 25 and redirected by a reflective mirror 22 configured for the emission wavelength of the Ti:sapphire pump source. Such pulses were further redirected by an off-axis parabolic mirror 20" having a predetermined N.A. sufficient to supply the necessary breakdown fluences and create a plasma site 18 and thus a desired structure (e.g., disk-like 32 or cone-like structures 34, as shown in FIG. 1) arranged in a predetermined coordinate in sample 28. Light originating from the waist of the beam was collected by this same off-axis parabolic mirror and upon creation of plasma site 18, a resultant broadband emission and in some scenarios a harmonic of pump source 8 is collected and substantially collimated by off-axis parabolic mirror 20" so as to be redirected along a broadband collected emission 26. Such collected emission 26 is reduced by about 15% due to the positioning of reflective mirror 22. The remainder of the broadband collected emission 26 is received by a second off-axis parabolic mirror 20' having a predetermined N.A. so as to enable focusing such collected emission through, for example, one or more configured filters 14 and through a collection slit 12' of a desired spectroscopic means 12. Such spectroscopic means 12, as shown in FIG. 1, can include, but are not limited to, a processor 2, spectroscopic processing software 3, a spectrometer, and/or any of the following detectors: an intensified charge coupled detector (ICCD), a time-gated intensified charge coupled detector (ICCD), a liquid nitrogen cooled CCD camera, a two-dimensional array detector, an avalanche CCD photodetector, a photomultiplier, or a photodiode, often in combination with predetermined optical filters 14 (e.g., notch filters to eliminate the pump source radiation, edge filters, and/or band-pass filters (e.g., band-pass having about 10 to 40 nm of bandwidth). The spectrometer itself for the experimental example arrangement included a grating blazed for 300 nm arranged to disperse the collected emission 26 with 5-nm spectral resolution. As part of the beneficial arrangement, an intensified charged coupled device 12" allowed the emission to be gated with 5-ns temporal resolution, which avoided the collection of long term microsecond deleterious thermal emission. The response of the system was calibrated with both black body and deuterium ($D_2$) light sources. Data was then automatically collected over a spectral range of 250 nm to 550 nm for each sample.

Figure 2:
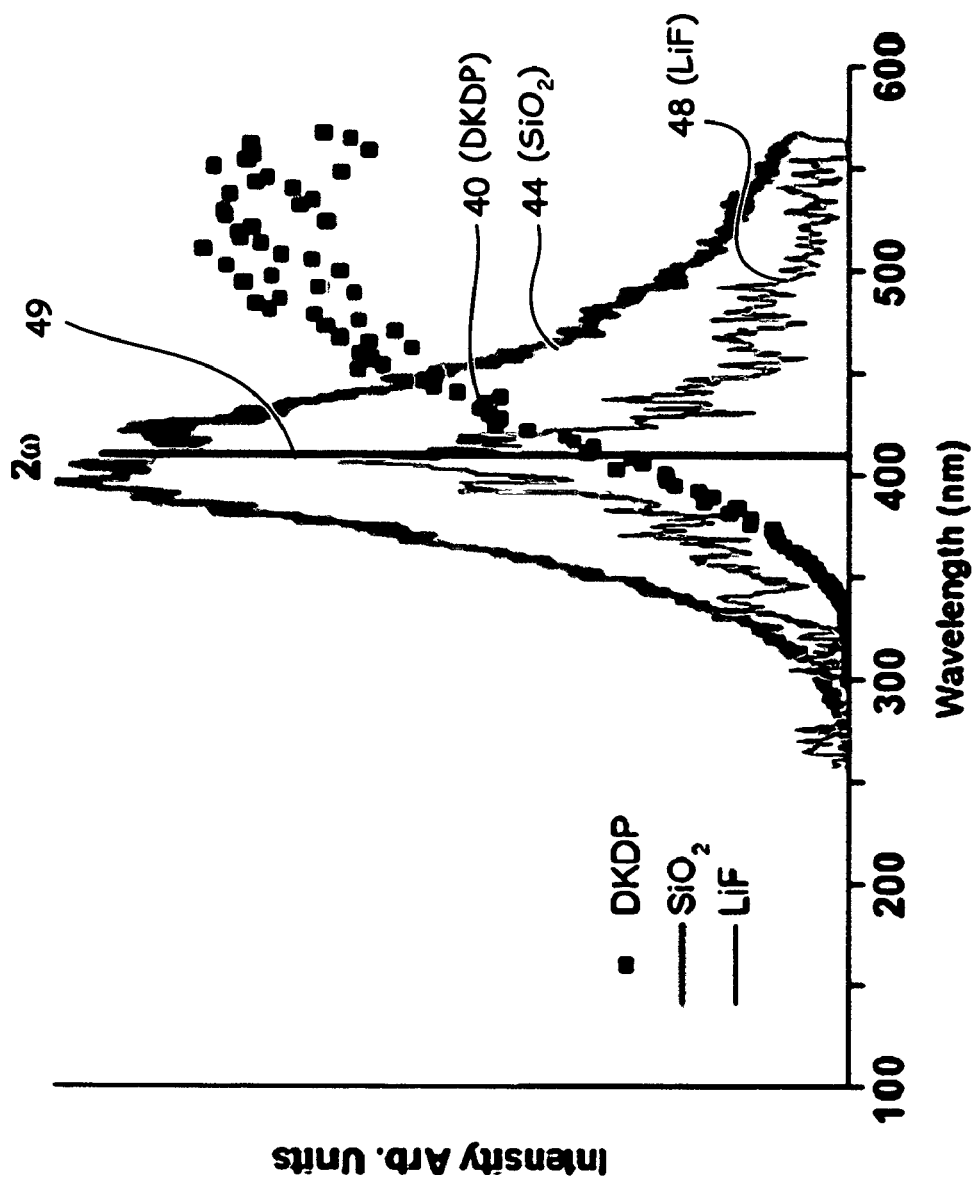
FIG. 2 shows collected experimental emission produced in SiO2, DKDP, and LiF using 820-nm, 150-fs pulses.

FIG. 2 shows collected experimental emission produced in SiO2 40, DKDP 44, and LiF 48 using 820-nm, 150-fs pulses.

The vertical line 49 denotes 410 nm (i.e., the second harmonic of 829 nm (2ω)). As shown in FIG. 2, emissions from 150-fs induced breakdown in $SiO_2$ and LiF have spectra that peak at about the second harmonic of the laser line (2ω), as indicated by the position of reference numeral 49) having a tail in the red part of the spectrum. However, the spectrum from DKDP is much broader and does not peak at 2ω. Such a difference in the spectra indicates a material dependence on the breakdown mechanism.

FIG. 3(a) shows emission from $Al_2O_3$ observed 70% 52 and 30% 54 of the time, respectively and corresponds to Plasma-induced Second Harmonic Generation (PSHG) and Bulk Emission (BE). The plurality of points 56 in inset FIG. 3(b) depict the difference of the two, and the solid curve 58 is a Gaussian fit. The fit is centered at 410.5 nm and has a full width half maximum (FWHM) of 59.9 nm. The vertical line 60 indicates 410 nm (i.e., twice the frequency of the laser line).

Most of the time (i.e., about 70% of the measured spectra) the spectra appeared qualitatively identical to those observed in SiO2 and LiF (peaked at 2ω with a tail to the red). However, about 30% of the spectra collected from Al2O3 lacked the 2ω peak entirely and included a broad spectrum trailing to the red. The difference spectrum 56, as shown in FIG. 3(b), obtained by subtraction of the two types of Al2O3 spectra is a Gaussian distribution centered at 2ω), indicating the participation of two distinct components in the observed spectra. The spectra are comprised of a component identical in form to that observed in SiO2 and LiF, together with a component qualitatively similar to that observed in KDP.

The peak in all three materials at 410 nm can be attributed to second-harmonic generation (SHG) from the 820-nm laser line due to induced critical-density plasma in forming structures of the present invention. The spectral profile obtained from DKDP 40, as shown in FIG. 2, did not exhibit the SHG peak at 410 nm, and it is qualitatively similar to the broad spectral component observed in Al2O3. The origin of the DKDP spectrum 40 as well as the second spectral component observed in Al2O3 (also somewhat present in SiO2 and LiF) can be attributed to self-focusing. Self focusing occurs when the power of the laser (P) exceeds a material-dependent critical power (Pcr), given by equation (1):

$$P_{cr}=3.77\lambda_0^2/8\pi n_0 n_2, \quad (1)$$

where λ is the free-space wavelength of the laser light and $n_0$ and $n_2$ are the linear and nonlinear indices of refraction, respectively.

One can understand the dependence of the emission spectra on Pcr, P, and (τ) the pulse width, by considering how the geometry of the ionized region is affected by such parameters. Damage produced by a fs pulse can assume two distinct morphologies, depending on the power of the pulse and the focal geometry. For fs laser pulses below Pcr, the initial breakdown is manifested as an ionized region in the shape of a disk less than 1 μm in thickness. The electron density in such a region reaches the critical density for the pump wavelength very quickly (compared with τ). The high electron density allows the pump radiation to penetrate only a short distance (the plasma skin depth), restricting expansion of the ionized region away from the site of initial breakdown by reflecting and scattering the incident laser light. The ionization waves for fs pulses (which propagate at velocities of the order of the sound speed in the material) have insufficient time to expand the ionized region, which remains a thin disk.

SHG of light from the interaction of laser pulses with plasma in the backscattering geometry is a well-known phenomenon. Near the critical-density points, energy from the incident laser radiation produces plasma waves that are due to linear or nonlinear processes. The second-harmonic radiation is produced by coupling of two plasma waves or plasma and electromagnetic waves and is often accompanied by spectral broadening from plasma turbulence.

The observed broadening has a dynamic nature associated with rapid changes in the electron density. The time scale for the increase in electron density from very low or no background density to critical density ($n_c$) is of the order of tens of fs. Moreover, such an increase electron density gives rise to a rapid change in the index of refraction of the ionized region and a high-velocity ionization front, both of which can contribute to the unexpected observed spectral broadening as disclosed herein. When the laser pulse is above Pcr, self-focusing and filamentation occur before the focus is reached and the breakdown morphology changes from a disk of high-electron-density plasma to filaments of relatively low electron density. The lower electron densities associated with filamentation do not allow light to excite plasma waves effectively, precluding SHG. However, this breakdown geometry, because of the interplay between self-focusing and multiphoton ionization, can result in white-light continuum generation.

Accordingly, two breakdown situations can be readily identified from the radiation produced during breakdown induced in a given sample. By monitoring the spectral characteristics, one can determine the mechanism of laser-induced breakdown, and hence its morphology, in real time. In addition, the ability to monitor and control the breakdown mechanism noninvasively allows modified material to be written in the different morphologies with increased precision as discussed above.

Applicants are providing this description, which includes drawings and examples of specific embodiments, to give a broad representation of the invention. Various changes and modifications within the spirit and scope of the invention will become apparent to those skilled in the art from this description and by practice of the invention. The scope of the invention is not intended to be limited to the particular forms disclosed and the invention covers all modifications, equivalents, and alternatives falling within the spirit and scope of the invention as defined by the claims.

The invention claimed is:

1. A spectroscopic feedback method for writing optical data, comprising:
    illuminating an interaction volume with predetermined laser optical intensities to define a plurality of data bits and thereby encode a data set; and
    spectroscopically real-time confirming a written bit status for each said defined bit of said data set.

2. The method of claim 1, wherein said real-time confirming comprises spectroscopic monitoring for predetermined spectral emission resulting from said predetermined intensities.

3. The method of claim 2, wherein said predetermined spectral emission comprises broadband emission.

4. The method of claim 2, wherein said predetermined spectral emission comprises a harmonic of a source configured to produce said predetermined intensities.

5. The method of claim 2, wherein said spectroscopic monitoring further comprises time-gated spectroscopy.

6. The method of claim 1, wherein said data bits comprise a predetermined morphology in said interaction volume.

7. The method of claim 6, wherein said predetermined morphology represents a digital 1 or a digital 0 selected from: an cone-like structure, a disk-like structure, or a non-structural change to said interaction volume.

8. The method of claim 6, wherein said digital 1 or said digital 0 can be optically read from at least one method comprising: laser differential interference contrast microscopy, confocal microscopy, and scattering microscopy.

9. The method of claim 6, wherein said predetermined morphology results from optically induced damage of a material.

10. The method of claim 9, wherein said optically induced damage results from predetermined laser intensities at about or greater than about a critical breakdown power (Pcr) for a given material.

11. The method of claim 9, wherein said optically induced damage comprises dielectric breakdown.

12. The method of claim 6, wherein said morphology comprises a refractive index inhomogeneity.

13. The method of claim 1, wherein said illuminating step further comprises arranging said predetermined laser intensities along predetermined X-Y-Z coordinates of said interaction volume to define a three dimensional array of bit locations.

14. The method of claim 13, wherein said three dimensional array of bit locations are arranged with a density of greater than $10^9$ per cubic centimeter.

15. The method of claim 1, wherein said predetermined laser intensities comprise directing one or more coherent light pulses via a focusing optic.

16. The method of claim 15, wherein said one or more coherent light pulses comprise pulse lengths greater than about 1 fs.

17. The method of claim 1, wherein said predetermined intensities comprise fluences of up to about 10 $J/cm^2$.

18. A spectroscopic feedback method for writing in an optical material, comprising:
    micromachining an interaction volume with a predetermined laser intensity; and
    spectroscopically confirming a desired morphology in real-time resulting from said predetermined laser intensity.

19. The method of claim 18, wherein said desired morphology results from predetermined laser intensities at about or greater than about a critical breakdown power (Pcr), for a given material.

20. The method of claim 18, wherein said desired morphology produced by said predetermined laser intensity comprises a refractive index inhomogeneity.

21. The method of claim 19, wherein said desired morphology comprises dielectric breakdown of said interaction volume.

22. The method of claim 18, wherein said micromachining step further comprises arranging said predetermined laser intensity along predetermined X-Y-Z coordinates of said interaction volume to define an optical channel.

23. The method of claim 18, wherein said predetermined laser intensities comprise directing one or more coherent light pulses through via a focusing optic.

24. The method of claim 23, wherein said one or more coherent light pulses comprise pulse lengths greater than about 1 fs.

25. The method of claim 18, wherein said predetermined intensities comprise fluences of up to about 10 $J/cm^2$.

26. The method of claim 18, wherein said spectroscopically monitoring step further comprises monitoring broadband emission.

27. The method of claim 18, wherein said spectroscopically monitoring step further comprises monitoring a harmonic of said laser source.

28. A spectroscopic feedback apparatus for confirming a desired morphology in a material, comprising:
    a material;
    a source of electromagnetic radiation configured to produce a desired morphology within an interaction volume of said material; and
    spectroscopic means to real-time monitor a characteristic spectral emission so as to confirm said desired morphology.

29. The apparatus of claim 28, wherein said spectroscopic means further comprises a spectrometer.

30. The apparatus of claim 28, wherein said spectroscopic means further comprises a computer configured with spectroscopic processing software.

31. The apparatus of claim 28, wherein said spectroscopic means further comprises one or more optical filters.

32. The apparatus of claim 28, wherein said spectroscopic means further comprises at least one detector selected from: an intensified charge coupled detector (ICCD), a time-gated intensified charge coupled detector (ICCD), a liquid nitrogen cooled CCD camera, a two-dimensional array detector, an avalanche CCD photodetector, a photomultiplier, and a photodiode.

33. The apparatus of claim 28, wherein said source of electromagnetic radiation comprises a pulsed laser source.

34. The apparatus of claim 33, wherein said pulsed laser source is arranged to produce said desired morphology along predetermined X-Y-Z coordinates of said interaction volume so as to define a three dimensional array of bit locations.

35. The apparatus of claim 34, wherein said desired morphology represents a digital 1 or a digital 0 selected from: a cone-like structure, a disk-like structure, or a non-structural change to said interaction volume.

36. The apparatus of claim 35, wherein said cone-like structure and said disk-like structure comprises dielectric breakdown.

37. The apparatus of claim 33, wherein said pulsed laser source is arranged to produce said desired morphology along predetermined X-Y-Z coordinates of said interaction volume to define an optical channel.

38. The apparatus of claim 28, wherein said desired morphology comprises a refractive index inhomogeneity.

39. The apparatus of claim 28, wherein said electromagnetic radiation source is configured to produce one or more pulses having pulse lengths greater than about 1 fs.

40. The apparatus of claim 28, wherein said electromagnetic radiation source is configured to produce fluences of up to about 10 $J/cm^2$.

41. The apparatus of claim 28, wherein said spectral breakdown emission comprises broadband emission.

42. The apparatus of claim 28, wherein said spectral breakdown emission comprises a harmonic of said electromagnetic radiation source.

43. The apparatus of claim 28, wherein said spectral breakdown emission comprises a wavelength of at least 250 nm.

44. The apparatus of claim 28, wherein said source of electromagnetic radiation is configured to produce predetermined laser intensities at about or greater than about a critical breakdown power (Pcr) for a given material so as to create a predetermined localized breakdown.

45. The apparatus of claim 28, wherein said material comprises a material transparent to a predetermined use wavelength.

* * * * *